(12) United States Patent
Park et al.

(10) Patent No.: US 11,543,330 B2
(45) Date of Patent: Jan. 3, 2023

(54) BIO SAMPLE COLLECTION DEVICE

(71) Applicant: BIONEER CORPORATION, Daejeon (KR)

(72) Inventors: Han Oh Park, Daejeon (KR); Jung Do Kim, Daejeon (KR)

(73) Assignee: BIONEER CORPORATION, Daejeon (KR)

( * ) Notice: Subject to any disclaimer, the term of this patent is extended or adjusted under 35 U.S.C. 154(b) by 441 days.

(21) Appl. No.: 16/651,584

(22) PCT Filed: Oct. 24, 2017

(86) PCT No.: PCT/KR2017/011750
§ 371 (c)(1),
(2) Date: Mar. 27, 2020

(87) PCT Pub. No.: WO2019/083052
PCT Pub. Date: May 2, 2019

(65) Prior Publication Data
US 2020/0256767 A1 Aug. 13, 2020

(51) Int. Cl.
*G01N 1/02* (2006.01)
*A61B 10/02* (2006.01)
*C12M 1/26* (2006.01)

(52) U.S. Cl.
CPC ............... *G01N 1/02* (2013.01); *A61B 10/02* (2013.01); *C12M 1/26* (2013.01)

(58) Field of Classification Search
CPC ...... G01N 1/02; A61B 10/02; A61B 10/0096; A61B 10/0038; B01L 2200/16; C12M 1/26
See application file for complete search history.

(56) References Cited

U.S. PATENT DOCUMENTS 6,277,646 B1 * 8/2001 Guirguis ................. B01L 3/502
422/417
8,597,954 B2 12/2013 Tanigami et al.
9,079,181 B2 * 7/2015 Curry .................... B01L 3/5029
(Continued)

FOREIGN PATENT DOCUMENTS

CN 112674802 A * 4/2021 ......... A61B 10/0038
EP 3967242 A1 * 3/2022 .............. B01L 3/502
(Continued)

OTHER PUBLICATIONS

Chinese Office Action for related CN Application No. 201780096175.9 dated May 26, 2022 from Chinese Intellectual Property Office.
(Continued)

*Primary Examiner* — Francis C Gray
(74) *Attorney, Agent, or Firm* — Paratus Law Group, PLLC (57) ABSTRACT

A bio sample collection device including: a housing; a cap part detachably fastened to the housing, and including a bio sample collector for collecting a bio sample; and a bio sample processing liquid storage unit storing bio sample processing liquid, the bio sample processing liquid storage unit being formed to be broken when the cap part is combined with the housing after bio sample is collected so that the bio sample processing liquid is mixed with the bio sample.

9 Claims, 9 Drawing Sheets

(56) References Cited

U.S. PATENT DOCUMENTS

| | | | |
|---|---|---|---|
| 2005/0112024 A1* | 5/2005 | Guo | ........................ B01L 3/502 422/562 |
| 2010/0000341 A1 | 1/2010 | Hasegawa et al. | |
| 2011/0060137 A1 | 3/2011 | Tanigami et al. | |
| 2016/0074022 A1 | 3/2016 | Oliva et al. | |

FOREIGN PATENT DOCUMENTS

| | | | |
|---|---|---|---|
| JP | H05-006367 U | 1/1993 | |
| JP | H08-015254 A | 1/1996 | |
| JP | H10-070974 A | 3/1998 | |
| JP | 2010-213660 A | 9/2010 | |
| KR | 10-0662124 B1 | 12/2006 | |
| KR | 20-0473307 Y1 | 6/2014 | |
| KR | 20-2016-0001613 U | 5/2016 | |
| WO | WO 2009/139317 A1 | 11/2009 | |
| WO | WO 2012/150713 A1 | 11/2012 | |
| WO | WO 2017/016676 A1 | 2/2017 | |
| WO | WO-2018027065 A1 * | 2/2018 | .............. B01L 3/502 |

OTHER PUBLICATIONS

International Preliminary Report on Patentability for PCT/KR2017/011750 dated Apr. 28, 2020 from the International Bureau of WIPO, including Written Opinion of the International Searching Authority dated Jul. 13, 2018 from Korean Intellectual Property Office.
International Search Report for PCT/KR2017/011750 dated Jul. 13, 2018 from Korean Intellectual Property Office.

* cited by examiner

BIO SAMPLE COLLECTION DEVICE

CROSS REFERENCE TO PRIOR APPLICATION

This application is a National Stage Patent Application of PCT International Patent Application No. PCT/KR2017/011750 (filed on Oct. 24, 2017) under 35 U.S.C. § 371, which is hereby incorporated by reference in its entirety.

BACKGROUND

The present invention relates to a sample collection device, and more particularly, to a bio sample collection device.

As the interest in health increases, a process of collecting and testing various bio samples in the vicinity is in progress. In addition to a process of collecting and inspecting sludge of the sewage treatment plant, as well as sampling the food samples for food poisoning test, samples of feces and the like for the health check is to proceed.

Since these bio samples are generally unhygienic, various studies are being conducted for hygienic collection. As a device for collecting such a bio sample, the Korean Utility Model Registration No. 20-0473307, "Feces Sampling Device" and the Korean Utility Model Publication No. 20-2016-0001613, "Feces sampling and inspection container" are disclosed.

However, these bio sample collection devices are focused only on hygienic collection, which is insufficient for post-collection processing. For example, in the case of conventional bio sample collection devices, when the feces are collected for the intestinal microorganism test, the collected feces are exposed to the air, thereby causing a change in the distribution of the intestinal microorganisms immediately after the collection. That is, there are aerobic and anaerobic microorganisms in the intestinal microorganisms. When they are exposed to air during their collection, which affects the survival of anaerobic and aerobic microorganisms, thus changing their distribution. Therefore, when the collection time is delayed until the test, the intestinal microbial distribution and population changes, which makes it difficult to make an accurate test for disease diagnosis and microbial measurement of an individual.

SUMMARY

Accordingly, the problem to be solved by the present invention is to provide a bio sample collection device that can more accurately perform the test for the bio sample.

A bio sample collection device according to an exemplary embodiment of the present invention for solving this problem includes a housing, a cap part and a bio sample processing liquid storage unit. The cap part is detachably fastened to the housing, and includes a bio sample collector for collecting a bio sample. The bio sample processing liquid storage unit stores bio sample processing liquid. The bio sample processing liquid storage unit is formed to be broken when the cap part is combined with the housing after bio sample is collected so that the bio sample processing liquid is mixed with the bio sample.

For example, the cap part and the housing may have screw thread corresponding to each other, so that the cap part is detachable by rotation to the housing. A stopper may be formed on the screw thread of the cap part and the housing, and the cap part and the housing may be fastened only to the stopper before the bio sample is collected, and the cap part and the housing may be completely fastened to each other through the stopper, after the bio sample is collected by the bio sample collector.

The cap part may include a covering part and a cylinder part. The covering part may be formed with the screw thread and fastened to the housing. The cylinder part may have an upper portion connected to a lower portion of the covering part and a lower portion opened. The bio sample collector may be movably combined to the cylinder part, so that the bio sample collector may be movable along the outer surface of the cylinder part up and down.

The lower portion of the cylinder part, which is opened, may be sealed by a sealing film, so that the bio sample processing liquid may be contained in the cylinder part to configure the bio sample processing liquid storage unit.

In this case, the bio sample collector may include a puncher, so that the puncher may punch the sealing film when the cap part and the housing are completely engaged, thereby introducing the bio sample processing liquid into the housing.

Alternatively, a lower portion of the housing may be covered by a sealing film, so that the bio sample processing liquid may be contained in the lower portion of the housing to configure the bio sample processing liquid storage unit.

In this case, the bio sample collector may punch the sealing film when the cap part and the housing are completely engaged, so that the bio sample processing liquid may be introduced into the housing.

On the other hand, the bio sample collector may include a plurality of protruding parts protruding toward a bottom of the housing.

Further, a pipette inlet, which is capable of being punched by a pipette, may be formed at an upper surface of the cap part.

In this case, the pipette inlet may be formed by at least two line segments crossing each other, of which thickness is thinner than the other areas.

As described above, the bio sample collection device according to the present invention is damaged when the cap part is fastened to the housing after the bio sample has been collected, and formed to mix the bio sample processing liquid with the bio sample, thereby improving accuracy of the inspection of the bio sample.

In addition, it is possible to ensure the safety of the user by preventing the bio sample processing liquid is exposed to the user before the bio sample is collected.

In addition, by forming a stopper on the screw thread of the cap part and the housing, it is possible to prevent the cap part is completely fastened to the housing before the sample is collected to damage the bio sample processing liquid storage unit.

In addition, when the bio sample collector includes a plurality of protruding parts protruding toward the lower surface of the housing, the protruding parts is lowered to collect bio samples so that the bio samples is kept between the protruding parts, thereby improving hygiene in comparison to a conventional collector with a spoon. In addition, when the cap part is rotated to be combined with the housing, the bio samples can be mixed with the bio sample processing liquid more effectively.

In addition, by forming a pipette inlet to be punched by the pipette on the upper surface of the cap part, it is possible to take a bio sample without opening the cap part, thereby enabling a more hygienic inspection.

In addition, when the pipette inlet is formed by at least two or more line segment areas crossing each other, of which thickness is thinner than other areas, the pipette inlet may be formed in the forming process of the cap part without any additional process.

DETAILED DESCRIPTION

The present invention is described more fully hereinafter with reference to the accompanying drawings, in which example embodiments of the present invention are shown. The present invention may, however, be embodied in many different forms and should not be construed as limited to the example embodiments set forth herein. Rather, these example embodiments are provided so that this disclosure will be thorough and complete, and will fully convey the scope of the present invention to those skilled in the art.

It will be understood that, although the terms first, second, third etc. may be used herein to describe various elements, components, regions, layers and/or sections, these elements, components, and/or sections should not be limited by these terms. These terms are only used to distinguish one element, component, region, layer or section from another region, layer or section. Thus, a first element, component, or section discussed below could be termed a second element, component, or section without departing from the teachings of the present invention.

The terminology used herein is for the purpose of describing particular example embodiments only and is not intended to be limiting of the present invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Also, A and B are 'connected' and 'coupled' means that in addition to A and B being directly connected or bonded, another component C may be included between A and B.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein. In addition, in the claims for the method invention, the steps may be reversed in order unless the steps are explicitly bound in order.

Hereinafter, preferred embodiments of the present invention will be described in detail with reference to the drawings.

Figure 1:
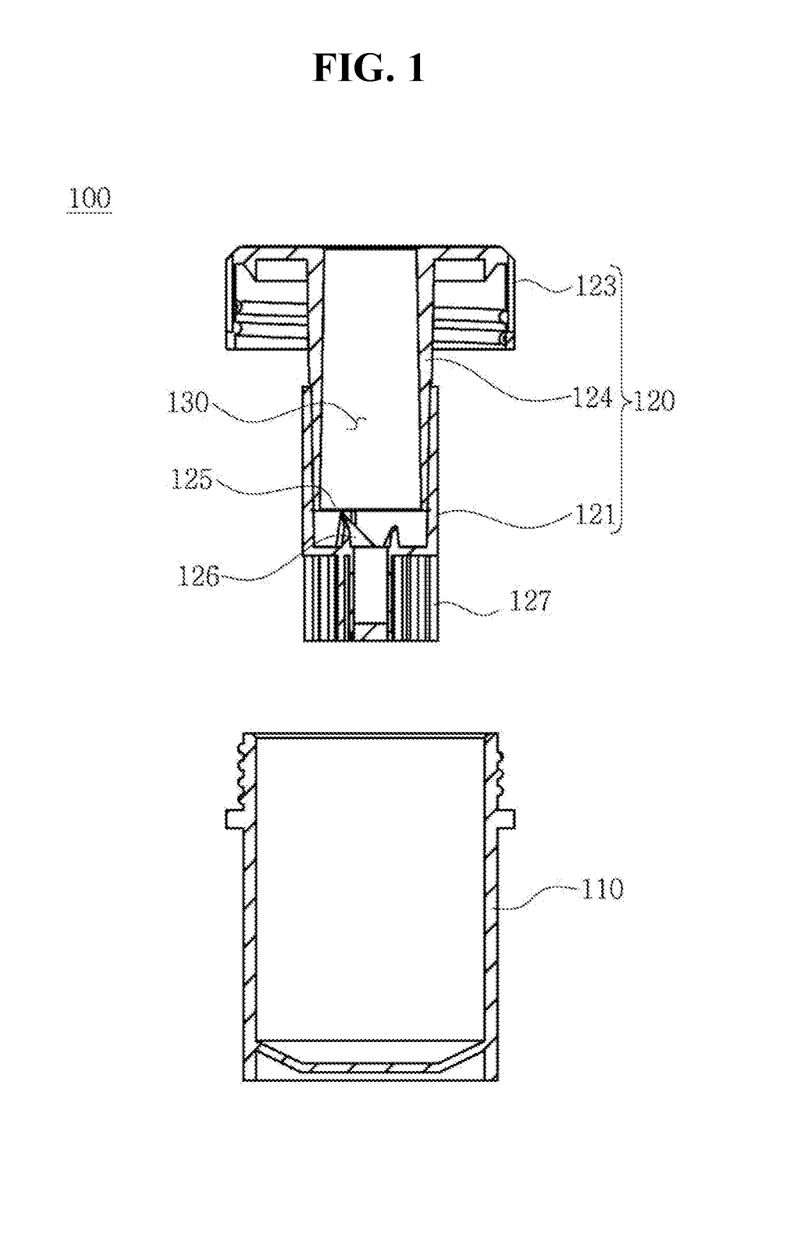
FIG. 1 is an exploded cross-sectional view of a bio sample collection device according to an exemplary embodiment of the present invention.
Figure 2:
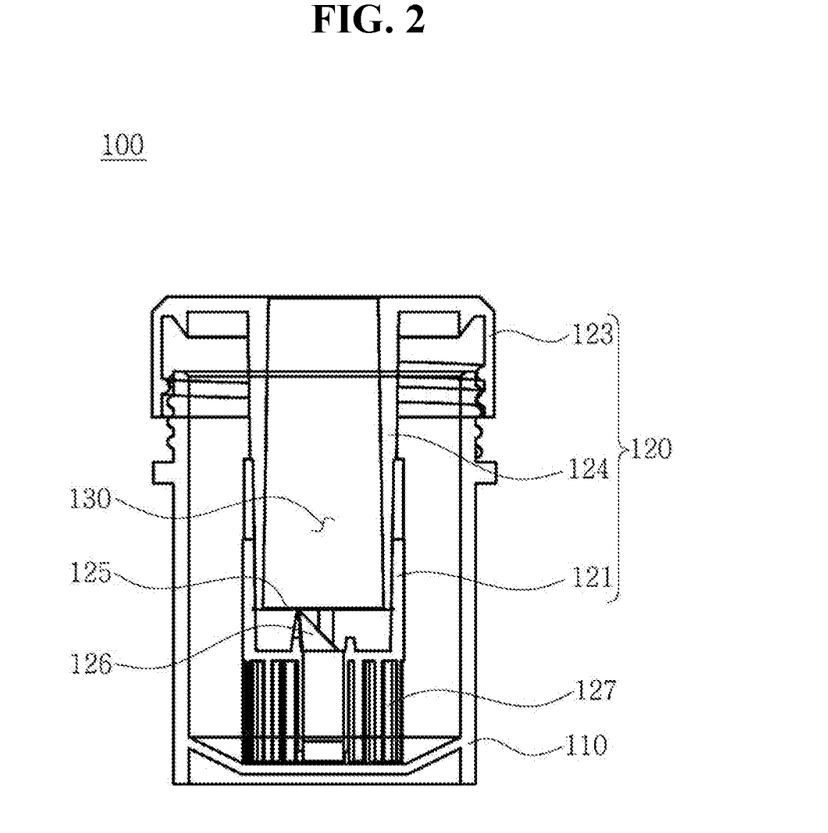
FIG. 2 is a cross-sectional view illustrating a state in which the cap part and the housing are fastened only to the stopper, before the bio sample collection device shown in FIG. 1 collects bio samples.
Figure 3:
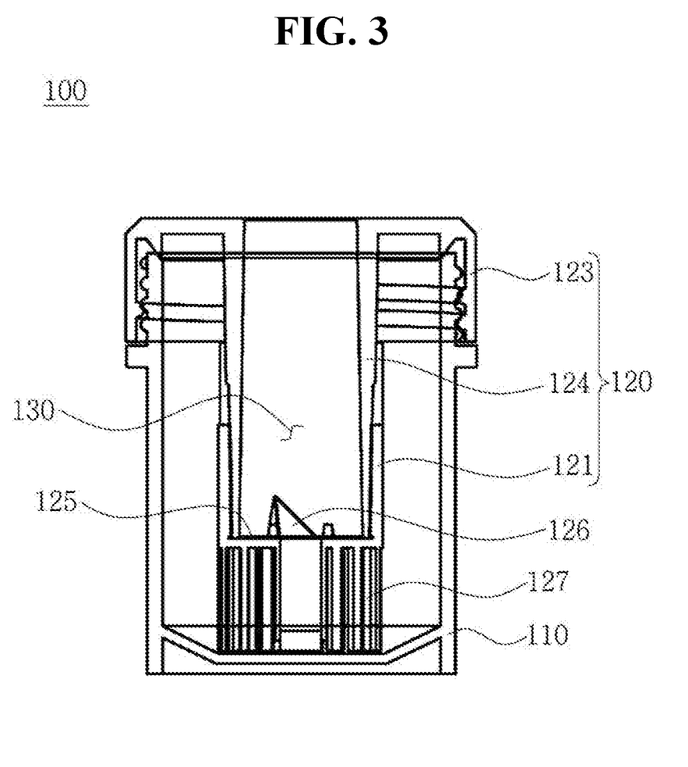
FIG. 3 is a cross-sectional view illustrating a state in which the cap part and the housing are completely fastened after the bio sample collection device illustrated in FIG. 1 collects bio samples.
Figure 4:
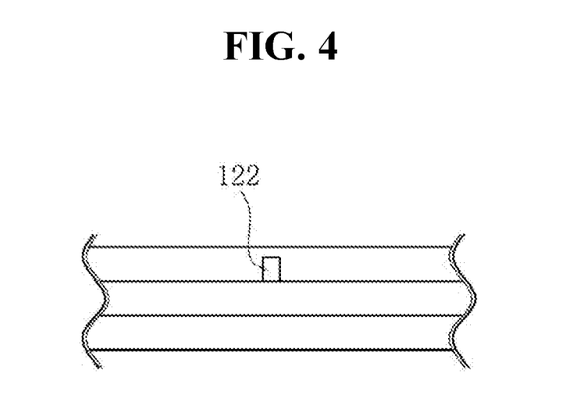
FIG. 4 is a conceptual view illustrating a stopper formed in a cap part and a housing of the bio sample collection device illustrated in FIG. 1.
Figure 5:
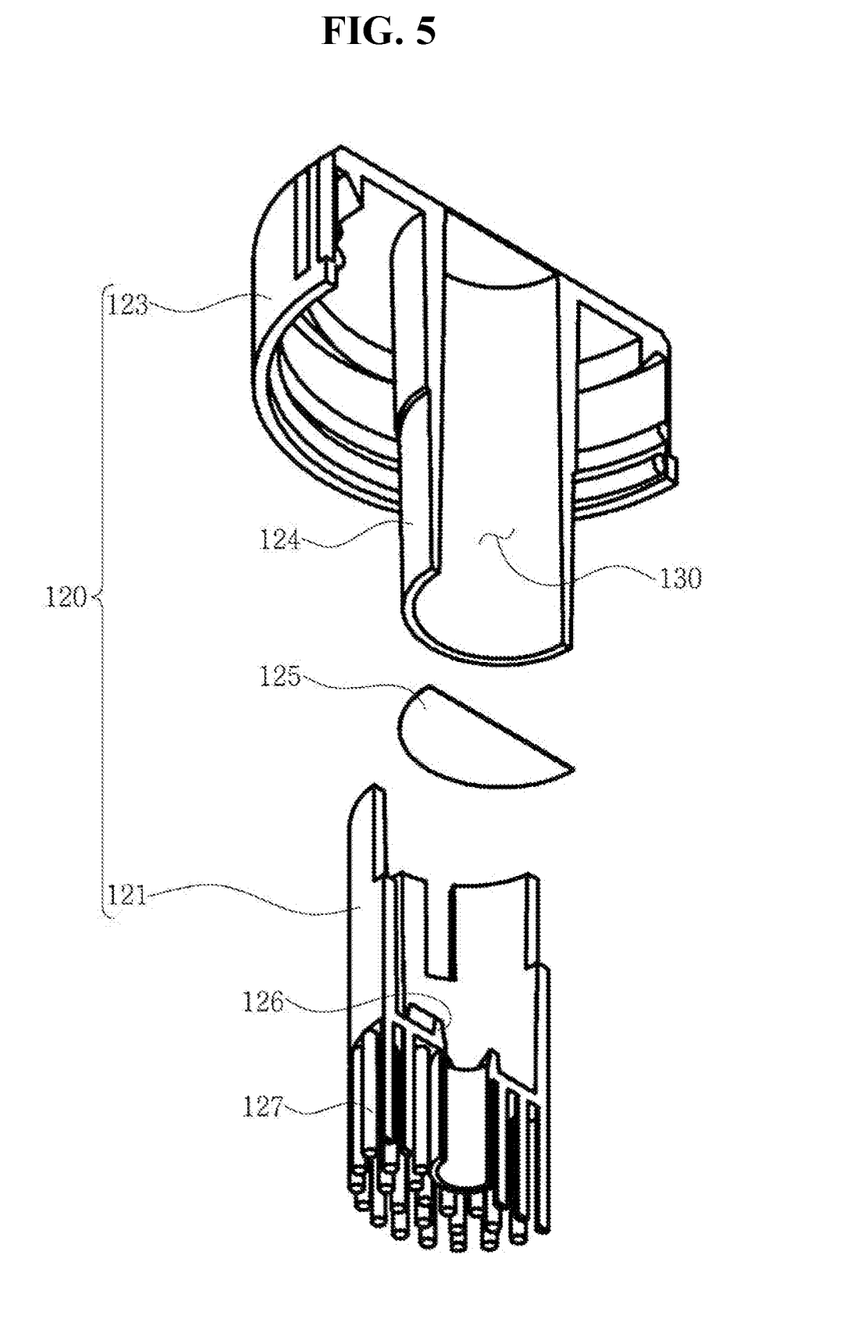
FIG. 5 is an exploded cut perspective view illustrating a cap part of the bio sample collection device illustrated in FIG. 1.

FIG. 1 is an exploded cross-sectional view of a bio sample collection device according to an exemplary embodiment of the present invention, and FIG. 2 is a cross-sectional view illustrating a state in which the cap part and the housing are fastened only to the stopper, before the bio sample collection device shown in FIG. 1 collects bio samples. FIG. 3 is a cross-sectional view illustrating a state in which the cap part and the housing are completely fastened after the bio sample collection device illustrated in FIG. 1 collects bio samples, FIG. 4 is a conceptual view illustrating a stopper formed in a cap part and a housing of the bio sample collection device illustrated in FIG. 1, and FIG. 5 is an exploded cut perspective view illustrating a cap part of the bio sample collection device illustrated in FIG. 1.

Referring to FIG. 1 to FIG. 5, a bio sample collection device 100 according to an exemplary embodiment of the present invention includes a housing 110, a cap part 120, and a bio sample processing liquid storage unit 130.

For example, the housing 110 may be formed in a cylindrical shape having a closed bottom, and the cap part 120 may also be formed in a cylindrical shape corresponding to the housing 110. For example, the housing 110 and the cap part 120 may be formed of plastic.

The cap part 120 is detachably fastened to the housing 110, and include a bio sample collector 121 for collecting a bio sample. The bio sample collector 121 is formed at, for example, a lower portion of the cap part 120, and when the cap part 120 is fastened to the housing 110, the bio sample collector 121 is inserted into the housing 110 not to be exposed to the outside. The bio sample collection device 100 with the bio sample collector 121 formed to the cap part 120 is more convenient, comparing to a bio sample collection device with a bio sample collector separately. That is, the bio sample collector 121 is separated by separating the cap part 120 from the housing 110, and when the cap part 120 is fastened to the housing 110 after the bio sample is collected, the bio sample collector 121 is inserted into the housing 110 to be hygiene.

On the other hand, the cap part 120 and the housing 110 are each formed with a screw thread corresponding to each other, the cap part 120 may be formed to be detachable by rotation to the housing 110.

The bio sample processing liquid storage unit 130 stores the bio sample processing liquid. The bio sample processing liquid may kill all of the microorganisms in the bio sample, or stop the activity of the microorganisms in order to ensure the accuracy of the test when the bio sample is examined. On the other hand, various kinds of bio sample processing liquid may be used depending on its purpose.

In this case, the bio sample processing liquid storage unit 130 is damaged when the cap part 120 is fastened to the housing 110 after the bio sample is collected by the bio sample collector 121, so that the bio sample processing liquid is mixed with the bio sample.

As described above, in the bio sample collection device 100 according to the present invention, when the cap part 120 is fastened to the housing 110 after the bio sample is collected, the bio sample processing liquid storage unit 130 is damaged, so that the bio sample processing liquid is mixed with the bio sample, thereby improving the accuracy of the test of the bio sample. For example, by inhibiting the relative disappearance and proliferation of the anaerobic microorganisms and aerobic microorganisms of feces, it is possible to accurately detect the type and distribution of anaerobic microorganisms and aerobic microorganisms.

On the other hand, when the bio sample processing liquid is placed inside the housing without any treatment, for example, the bio sample processing liquid may leak out when the cap part 120 is separated. In this case, when the bio sample processing liquid is harmful to the human body, the human body may be damaged. However, in the present invention, after the bio sample is collected, when the cap part 120 is fastened to the housing 110, the bio sample processing liquid storage unit 130 is broken, so that the bio sample processing liquid is mixed with the bio sample, thereby preventing the bio sample processing liquid from being exposed to a user before the bio sample is collected, thereby ensuring the safety of the user.

Meanwhile, as shown in FIG. 4, a stopper 122 is formed on the screw thread of the cap part 120 and the housing 110. As shown in FIG. 2, the cap part 120 and the housing 110 are engaged only to the stopper 122 before bio samples are collected, and as shown in FIG. 3, the cap part 120 and the housing 110 are completely engaged through the stopper 122 after bio samples are collected.

The stopper 122 may be formed in a linear shape, for example, as shown in FIG. 4, so that the stopper 122 may be broken when a user strongly rotates the cap part 120. Alternatively, the stopper 122 may be formed to have a locking step with rounded shape so as to pass through the locking step.

As such, when the stopper is formed on the screw thread of the cap part 120 and the housing 110, it can be prevented that the cap part 120 is completely fastened to the housing 110 and the bio sample processing liquid storage unit 130 is damaged before collecting bio sample.

The cap part 120 may include a covering part 123 and a cylinder part 124. The covering part 123 may be formed with the screw thread and may be fastened to the housing 110.

The cylinder part 124 may have an upper portion connected to a lower portion of the covering part 123 and a lower portion thereof may be opened. For example, the cylinder part 124 may have an upper portion integrally formed with the covering part 123, or may be separately formed and fastened to the covering part 123. For example, the cylinder part 124 may be formed in a cylindrical shape with an open bottom.

In addition, the open bottom of the cylinder part 124 is sealed by a sealing film 125, so that the bio sample processing liquid is contained in the cylinder part 124 so that the bio sample processing liquid storage unit 130 can be configured.

Meanwhile, the bio sample collector 121 may be movably engaged to the cylinder part 124, so that the bio sample collector 121 may move upward or downward along the outer surface of the cylinder part 124. To this end, an upper portion of the bio sample collector 121 may be formed in a cylindrical shape with open top, and a lower portion of the bio sample collector 121 may include a plurality of protruding parts 127 protruding toward the lower surface of the housing. As such, when the bio sample collector includes a plurality of protruding parts protruding toward the lower surface of the housing, the protruding parts is lowered to collect bio samples so that the bio samples is kept between the protruding parts, thereby improving hygiene in comparison to a conventional collector with a spoon. In addition, when the cap part is rotated to be combined with the housing, the bio samples can be mixed with the bio sample processing liquid more effectively.

On the other hand, the bio sample collector 121 includes a puncher 126. When the cap part 120 and the housing 110 are fully engaged, the bio sample collector 121 ascends along an outer surface of the cylinder part 124, so that the puncher 126 punches the sealing film 125, thereby allowing the bio sample processing liquid to flow into the housing 110. In this case, the bio sample processing liquid may flow through a gap between the outer surface of the cylinder part 124 and the inner surface of the bio sample collector 121. Alternatively, a separate through hole may be formed in the bio sample collector 121, and the bio sample processing liquid may flow out through the through hole.

Figure 6:
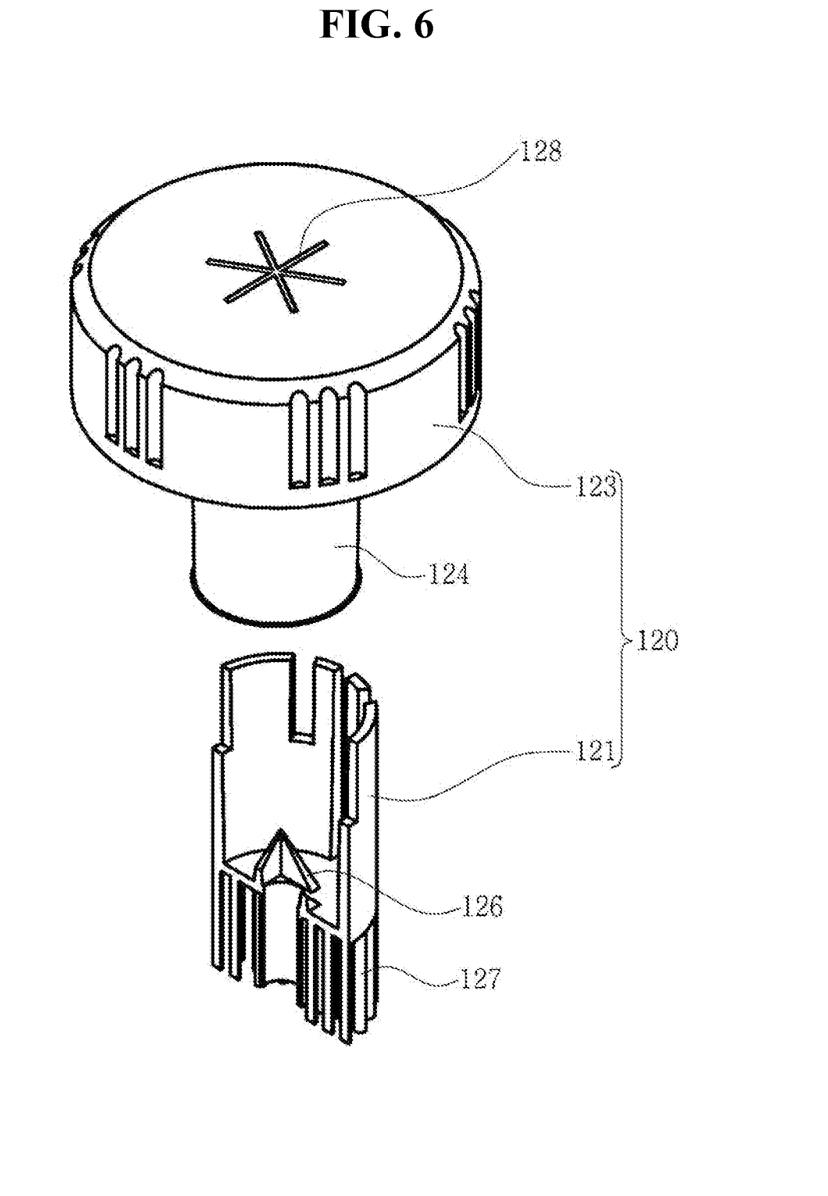
FIG. 6 is an exploded perspective view illustrating a cap part of the bio sample collection device illustrated in FIG. 1.
Figure 7:
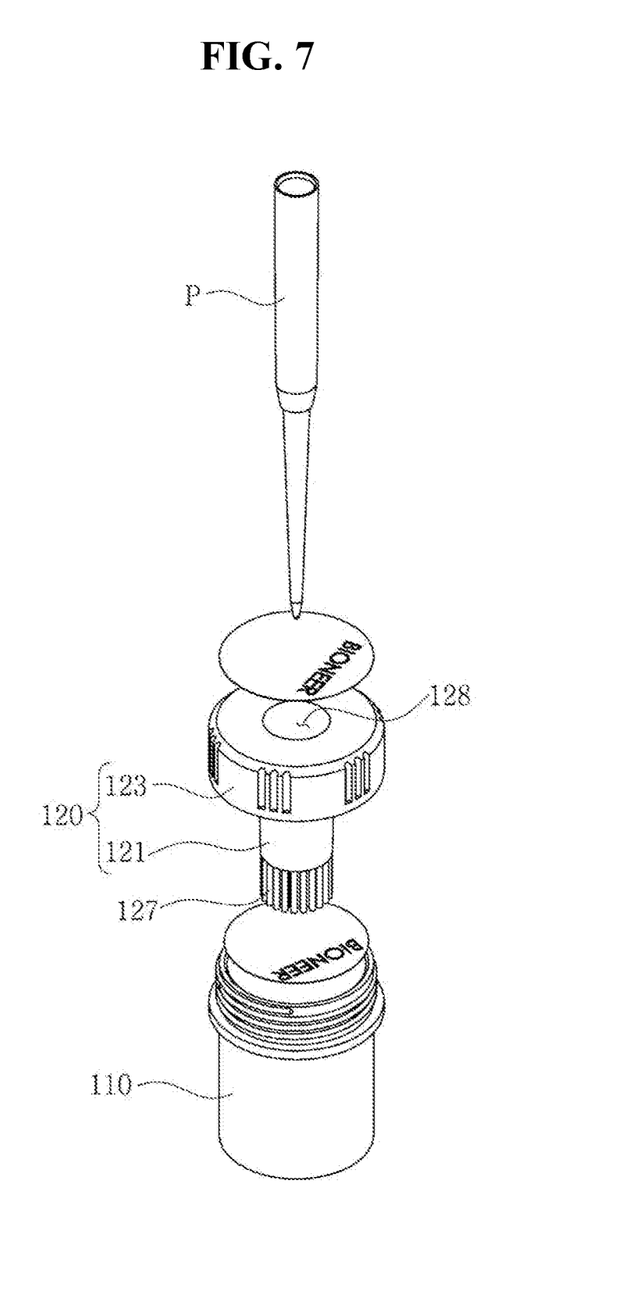
FIG. 7 is a perspective view illustrating the concept of inserting a pipette.
Figure 8:
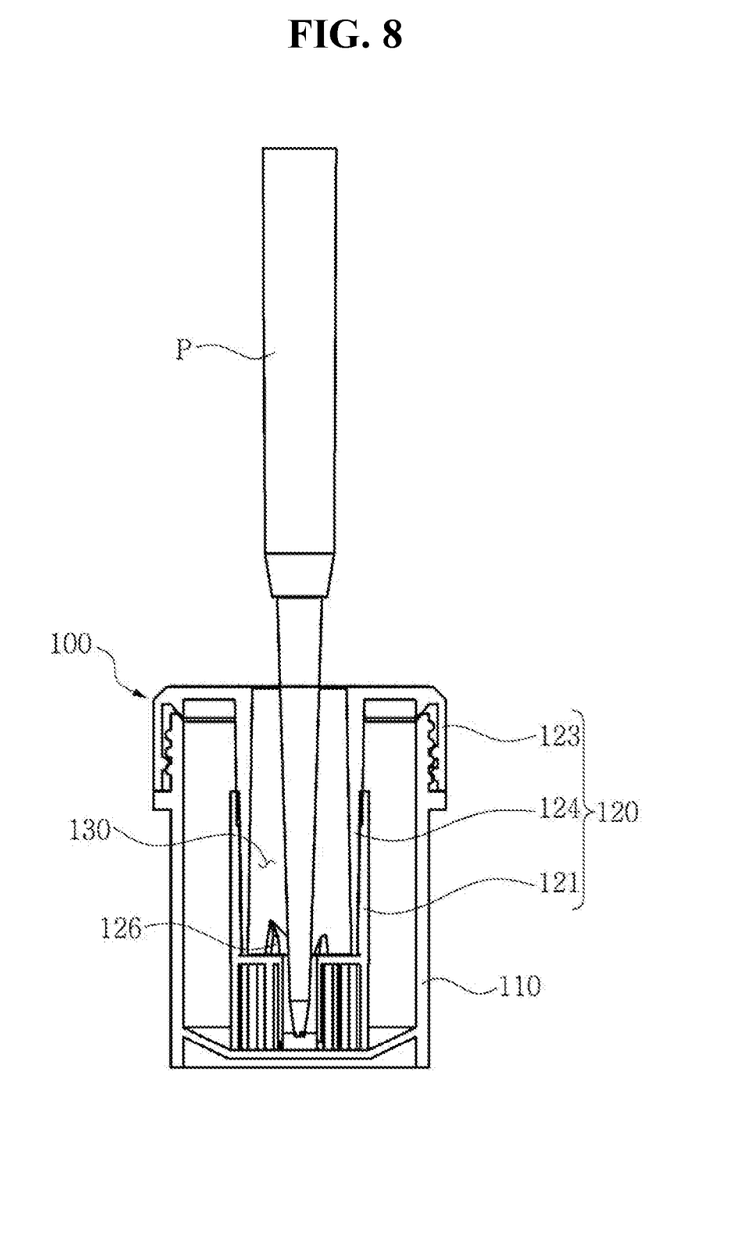
FIG. 8 is a cross-sectional view showing a state in which the pipette shown in FIG. 7 is inserted to perform an extraction process.

FIG. 6 is an exploded perspective view illustrating a cap part of the bio sample collection device illustrated in FIG. 1, FIG. 7 is a perspective view illustrating the concept of inserting a pipette, and FIG. 8 is a cross-sectional view showing a state in which the pipette shown in FIG. 7 is inserted to perform an extraction process.

Referring to FIG. 6, a pipette inlet 128 may be formed on an upper surface of the cap part 120 to be punched by the pipette. In more detail, the pipette inlet 128 is formed at the center of the covering part 123 of the cap part 120.

For example, the pipette inlet 128 may be formed by at least two line segment regions crossing each other, which have relatively thinner thickness than other regions of the cap part 120. That is, the pipette inlet 128 may be formed of three line segments that cross each other, as shown in FIG. 6, and the thickness of the three line segment regions is thinner than other regions to form the pipette inlet 128.

Alternatively, the pipette inlet 128 may be formed by a circular area with relatively thinner thickness than other regions of the covering part 123 as shown in FIG. 7.

However, it is more preferable that the pipette inlet 128 is formed by at least two line segment regions crossing each other, which have relatively thinner thickness than other regions of the cap part 120, because after the pipette (P) is inserted to collect the bio sample, and after the pipette (P) is separated from the cap part 120, an open area of the cap part 120 can be minimized thereby minimizing an outflow of bio sample.

As such, when the pipette inlet 128 is formed on the upper surface of the cap part 120 to be punched by the pipette P, the bio sample can be collected without opening the cap part 120, so that hygienic inspection is possible.

Figure 9:
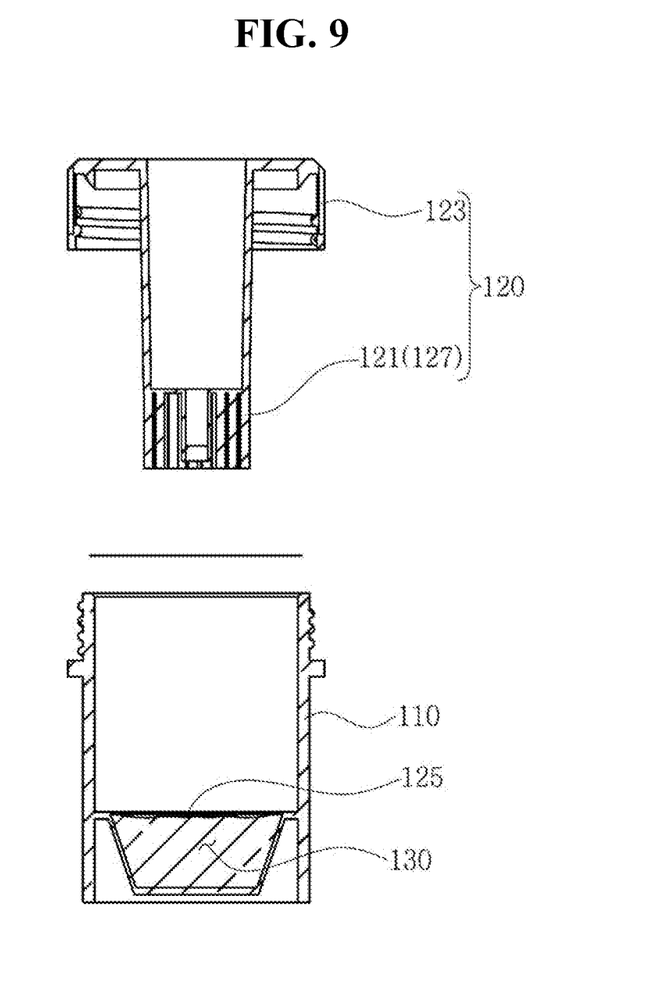
FIG. 9 is an exploded cross-sectional view illustrating a bio sample collection device according to another exemplary embodiment of the present invention.
Figure 10:
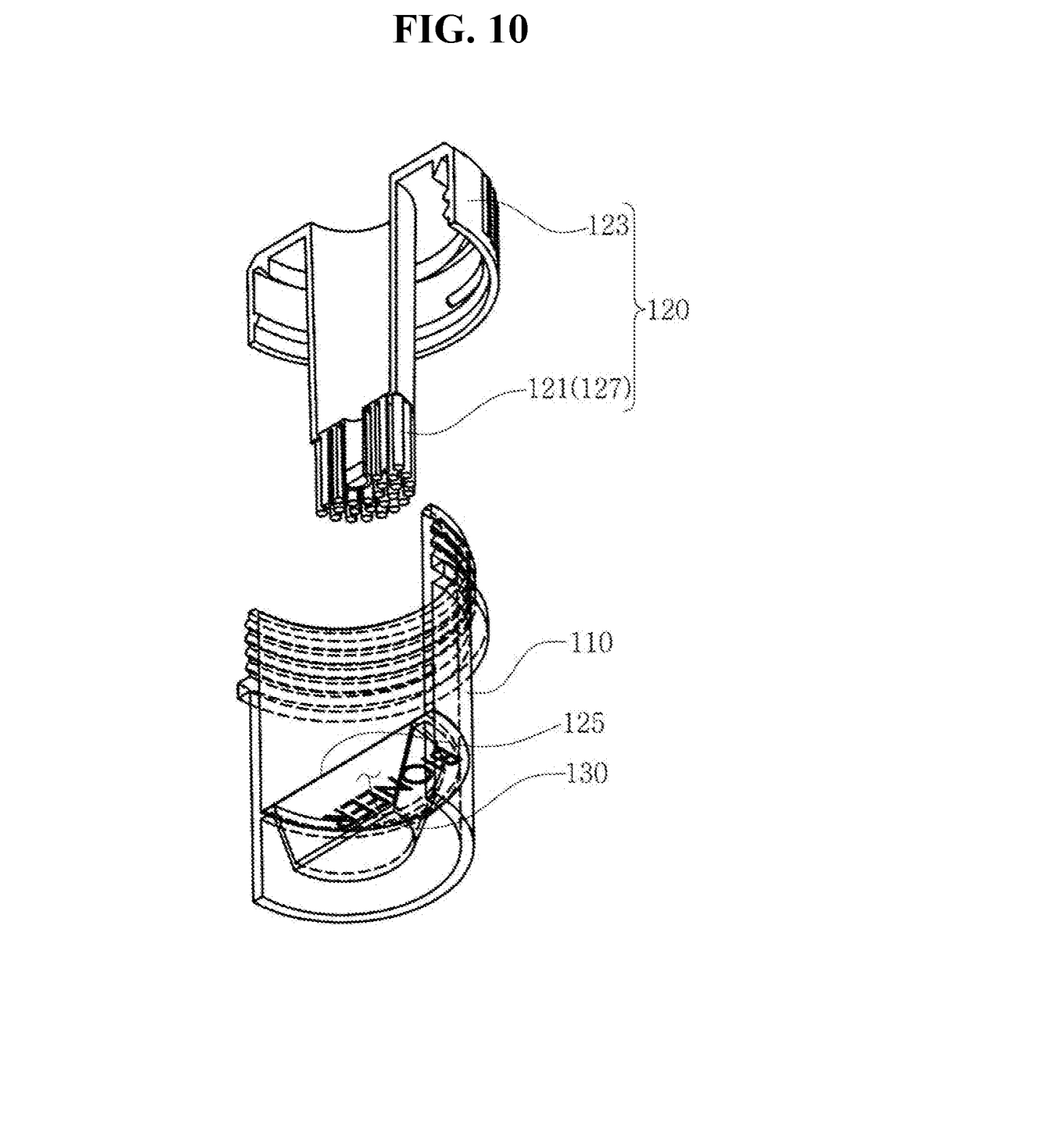
FIG. 10 is an exploded cut perspective view illustrating a cap part of the bio sample collection device illustrated in FIG. 9.

FIG. 9 is an exploded cross-sectional view illustrating a bio sample collection device according to another exemplary embodiment of the present invention, and FIG. 10 is an exploded cut perspective view illustrating a cap part of the bio sample collection device illustrated in FIG. 9. The bio sample collection device illustrated in FIGS. 9 to 10 is substantially the same except for the configuration of the bio sample processing liquid storage unit as compared to the bio sample collection device illustrated in the above embodiment. Therefore, the same or similar components bear the same reference numerals, and redundant descriptions are omitted.

Referring to FIG. 9 and FIG. 10, a bio sample collection device 100 according to another exemplary embodiment of the present invention includes a housing 110, a cap part 120, and a bio sample processing liquid storage unit 130.

A lower portion of the housing 110 may be covered by a sealing film 125 to contain the bio sample processing liquid in the lower portion of the housing 110 to form the bio sample processing liquid storage unit 130.

In this case, when the cap part 120 and the housing 110 are completely fastened, the bio sample collector 121 formed on the upper cap part 120 punches the sealing film 125, thereby introducing the bio sample processing liquid into the housing 110.

As described above, the bio sample collection device 100 according to the embodiments of the present invention is damaged when the cap part 120 is fastened to the housing 110 after the bio sample is collected, thereby mixing the bio sample processing liquid with the bio sample to improve the accuracy of the test of the bio sample.

Although the present invention has been described in the detailed description of the invention with reference to exemplary embodiments of the present invention, it will be understood to those skilled in the art that various modifications and variation can be made in the present invention without departing from the spirit or scope of the invention.

The invention claimed is:

1. A bio sample collection device comprising:
   a housing;
   a cap part detachably fastened to the housing, and including a bio sample collector for collecting a bio sample; and
   a bio sample processing liquid storage unit storing bio sample processing liquid, the bio sample processing liquid storage unit being formed to be broken when the cap part is combined with the housing after bio sample is collected so that the bio sample processing liquid is mixed with the bio sample,
   wherein the bio sample collector comprises a plurality of protruding parts protruding toward a bottom of the housing.

2. The bio sample collection device of claim 1, wherein the cap part and the housing have screw thread corresponding to each other, so that the cap part is detachable by rotation to the housing,
   a stopper is formed on the screw thread of the cap part and the housing, and the cap part and the housing are fastened only to the stopper before the bio sample is collected, and
   the cap part and the housing are completely fastened to each other through the stopper, after the bio sample is collected by the bio sample collector.

3. The bio sample collection device of claim 2, wherein the cap part comprises:
   a covering part formed with the screw thread and fastened to the housing; and
   a cylinder part having an upper portion connected to a lower portion of the covering part and having a lower portion opened, wherein the bio sample collector is movably combined to the cylinder part, so that the bio sample collector is movable along the outer surface of the cylinder part up and down.

4. The bio sample collection device of claim 3, wherein the lower portion of the cylinder part, which is opened, is sealed by a sealing film, so that the bio sample processing liquid is contained in the cylinder part to configure the bio sample processing liquid storage unit.

5. The bio sample collection device of claim 4, wherein the bio sample collector comprises a puncher, so that the puncher punches the sealing film when the cap part and the housing are completely engaged, thereby introducing the bio sample processing liquid into the housing.

6. The bio sample collection device of claim 2, wherein a lower portion of the housing is covered by a sealing film, so that the bio sample processing liquid is contained in the lower portion of the housing to configure the bio sample processing liquid storage unit.

7. The bio sample collection device of claim 6, wherein the bio sample collector punches the sealing film when the cap part and the housing are completely engaged, so that the bio sample processing liquid is introduced into the housing.

8. A bio sample collection device comprising:
   a housing;
   a cap part detachably fastened to the housing, and including a bio sample collector for collecting a bio sample; and
   a bio sample processing liquid storage unit storing bio sample processing liquid, the bio sample processing liquid storage unit being formed to be broken when the cap part is combined with the housing after bio sample is collected so that the bio sample processing liquid is mixed with the bio sample,
   wherein a pipette inlet, which is capable of being punched by a pipette, is formed at an upper surface of the cap part.

9. The bio sample collection device of claim 8, wherein the pipette inlet is formed by at least two line segments crossing each other, of which thickness is thinner than the other areas.

* * * * *